(12) United States Patent
Migliari

(10) Patent No.: US 6,808,487 B2
(45) Date of Patent: Oct. 26, 2004

(54) IMPLANT FOR HOLDING THE FEMALE BLADDER

(76) Inventor: Roberto Migliari, Via V. Carpacio 9, Arezzo (IT), I-52100

( * ) Notice: Subject to any disclaimer, the term of this patent is extended or adjusted under 35 U.S.C. 154(b) by 0 days.

(21) Appl. No.: 10/399,792

(22) PCT Filed: Oct. 31, 2001

(86) PCT No.: PCT/EP01/12638
§ 371 (c)(1),
(2), (4) Date: Sep. 25, 2003

(87) PCT Pub. No.: WO02/38079
PCT Pub. Date: May 16, 2002

(65) Prior Publication Data
US 2004/0116774 A1 Jun. 17, 2004

(30) Foreign Application Priority Data
Nov. 13, 2000 (DE) .......................... 100 56 169

(51) Int. Cl.[7] .................................. A61F 2/02
(52) U.S. Cl. ........................... 600/30; 600/37
(58) Field of Search ............... 600/29–31, 37; 128/DIG. 25, 885, 887; 606/151–158; 623/3.1, 3.29, 11.11, 23.64–23.65, 23.72, 924–926; 602/4–6; D3/201, 213–216; 2/44–45

(56) References Cited

FOREIGN PATENT DOCUMENTS

| DE | 195 44 162 C1 | 4/1997 |
| FR | 2 785 521 A1 | 5/2000 |
| WO | WO 01 06951 A1 | 2/2001 |

OTHER PUBLICATIONS

PCT International Search Report for PCT/EP 01/12638 mailed May 31, 2002.

Primary Examiner—John P. Lacyk

(57) ABSTRACT

An implant (1) for holding the female bladder has an areal, flexible basic structure (2), which has a base (4) with a front area (6), a rear area (8) and a longitudinal axis (L) running from front to back, as well as two extensions (10, 11). The two extensions (10, 11) start from the front area (6) of the base (4) and extend forwards, the distance between them increasing. Furthermore, two front supports (22, 23) which start from the free end areas of the two extensions (10, 11) and extend transverse to the longitudinal axis (L) of the base (4), and a connection (26) between the free end areas of the two extensions (10, 11) are provided. A free space (28) is formed between the connection (26), the two extensions (10, 11) and the base (4). Two rear supports (32, 33) start from opposite sides in the rear area (8) of the base (4) and extend transverse to the longitudinal axis (L) of the base (4).

19 Claims, 2 Drawing Sheets

IMPLANT FOR HOLDING THE FEMALE BLADDER

FIELD OF THE INVENTION

The invention relates to an implant for holding the female bladder, which can be used in particular for, treating a cystocele (cystoptosis) in association with stress incontinence.

BACKGROUND

To treat a cystocele, it is customary to suspend the bladder of a patient in a surgical procedure at four points using sutures. Two front sutures are made at the pubo-cervical fascia and the urethro-pelvic ligament, by which the bladder neck is held, whilst two rear sutures relate to the cardial ligaments and, if possible, the utero-sacral ligament, by which the bladder base is held. The bladder then comes to rest on the extended pubo-cervical or vesico-pelvic fascia. Such a surgery is costly, however, and stressful for the patient.

An implant is known from DE 195 44 162 C1 for suspending the female bladder in the case of bladder incontinence, which has an areal, flexible basic structure. Two first extensions and two second extensions start from a triangle-like-to-oblong-oval base. The two first extensions run on opposite sides of the longitudinal axis of the base, as do the two second extensions which are, however, aligned opposite to the two first extensions.

After such an implant has been inserted in open surgery, the bladder rests over a wide area of the implant, which enables a stable bilateral fixing of the bladder to be achieved both in the bladder neck area and the bladder vertex area. However, in this case the surgical procedure is also expensive and can be stressful for the patient.

A surgical instrument for treating female incontinence is described in WO 96/06567 and WO 97/13465, in which a strong bent surgical needle is attached to both ends of a tape made of polypropylene, which is guided using a detachable grip. The two needles are guided on opposite sides of the urethra of a patient via the vagina along the rear of the pubic bone to the outside of the abdominal wall. The tape comes to rest in a bend below the urethra. The two ends of the tape are pulled through the abdominal wall and cut off. They do not normally need to be sewn up, as the tape grows into the tissue relatively quickly. In the area of the urethra, the tape acts as a support without directly touching the urethra. The surgery is facilitated if the tape is provided with two covers which increase the sliding capacity in the tissue and are removed from the tape at the end of the surgery via the two outlets of the tape. With this method, bladder incontinence can be treated quickly, effectively and causing little stress. However, the method does not help in the case of a cystoptosis.

The object of the invention is to provide a possibility with which a cystocele which is associated with stress incontinence can be treated quickly, effectively and causing little stress to the patient.

SUMMARY OF THE INVENTION

This object is achieved by an implant for holding the female bladder with the features of claim 1. Advantageous versions of the invention emerge from the dependent claims.

The implant according to the invention for holding the female bladder has an areal, flexible basic structure which has a base and two extensions. The base contains a front area and a rear area and has a longitudinal axis running from the front (anterior) to the rear (posterior). The two extensions start from the front area of the base and extend forwards, the distance between them increasing. Two front supports start from the free end areas of the two extensions and extend transversely with respect to the longitudinal axis of the base. There is a connection between the free end areas of the two extensions, a free space being formed between the connection, the two extensions and the base. Furthermore, two rear supports are provided which start from opposite sides in the rear area of the base and extend transversely with respect to the longitudinal axis of the base.

When the implant is inserted into a patient, the connection and the two front supports support the central urethra without lying directly against it, similar to what is known from WO 96/06567 and WO 97/13465. The front part of the bladder is also held via the two extensions and the front area of the base. The bladder neck lies in the free area between the connection, the two extensions and the base and thus has a freedom of movement such as is required for micturition. The two rear supports and the rear area of the base serve to support the bladder base. Whilst the two front supports are preferably guided relatively loose in the implanted state, the two rear supports can be taut in order to lift the bladder base up to the extent that a cystoptosis is eliminated. Using the implant according to the invention, stress incontinence and a cystocele can thus be treated simultaneously.

The implant according to the invention can be inserted relatively easily via the vagina, as described in more detail below. Essentially the same effect is thus achieved as with the operation technique mentioned at the outset in which fascia and ligaments are tightened by four sutures, but in a manner that is less stressful for the patient. The surgical procedure can be carried out under local anaesthetic, is relatively swift and entails less post-operative pain. The implant also ensures a long-lasting and secure holding of the bladder. Using the two front supports and the two rear supports, the support of the urethra and of the bladder base can be optimized.

Preferably, the base has a concavely rounded front edge which merges in a U-shape into the two extensions. This design is particularly advantageous for guaranteeing the bladder neck the required freedom of movement. Via the two front supports and the connection, the central urethra can be nevertheless supported, such that a bladder incontinence is effectively treated.

In a preferred version of the implant, the rear area of the base extends behind the two rear supports and there preferably has a convexly rounded rear edge. This zone enables an enterocele (intestinal hernia) to be treated (or an enterocele to be prevented) by closing the recto-vaginal sack. If necessary, this area of the base can be cut to size shortly before the surgery or during the surgery so that it is optimally matched to the anatomy of the patient. If it is not required, it can also be separated completely from the rest of the implant.

The implant can be supplied together with two surgical needles, one needle being attached to the free end of one front support and to the free end of the rear support located on the same side of the longitudinal axis of the base, whilst the other needle is attached to the free end of the other front support and to the free end of the other rear support. These surgical needles are preferably designed as strong bent needles and can be used with the help of additional gripping parts, similar to what is known from WO 96/06567 and WO 97/13465. In the case of the implant according to the invention, however, each needle is connected not only to one tape end but to two supports, namely one of the front and one of the rear supports. In this way, upon guiding of the needle through the tissue, the front support and the rear support can simultaneously be pulled into the tissue on one side of the implant. This facilitates and shortens the surgery and is advantageous for the patient because of the smaller number of puncture points.

Preferably, the two front supports and two rear supports are provided with movable covers. These covers are preferably made of smooth plastics material, e.g. of polyethylene or polypropylene film material, so that they facilitate the pulling-through of the front supports and the rear supports through tissue. As soon as the implant as reached its proposed position, the covers can be removed via the free ends of the front supports and the rear supports and therefore do not remain in the patient's body.

The two front supports are preferably marked in a different colour from the two rear supports. In this way, the surgeon can distinguish with certainty the free ends of the supports pulled through the tissue and therefore knows precisely on which support he must pull if necessary in order to position the implant more precisely. The marking can be carried out by colouring the supports concerned, alternatively by colouring the associated covers.

In a preferred version of the invention, the two front supports and the connection are made in one piece as a front tape. Correspondingly, the two rear supports can also be made in one piece as a rear tape. In principle, tapes such as are known from WO 96/06567 and WO 97/13465 can be used for this. This version is advantageous as the tapes are suitable for absorbing tensile forces and in this case the two front supports or the two rear supports lie in a line so that the flexible basic structure of the implant must withstand only relatively small forces. The basic structure can therefore be light and made using little material, weilch is favourable for the patient.

Preferably, the front tape is guided through a slot in the free end area of one extension and through a slot in the free end area of the other extension. Correspondingly, the rear tape can be guided through two slots in the rear area of the base. This design enables the front and/or rear tape to be moved relative to the flexible basic structure during the surgery, which can be of help when positioning the implant. If this adjustment possibility is not required or not desired, the front and/or rear tape can be connected to the flexible basic structure in some other way, e.g. by sewing or welding.

The front tape is preferably shorter than the rear tape. This is particularly advantageous when a surgical needle is connected to the ends of two supports or tapes in the manner outline above, as it is thus taken into account that the rear tape runs over a greater length within the body of the patient than does the front tape.

The flexible basic structure preferably contains a weft-knitted or warp-knitted fabric. Suitable as materials are, in particular, non-resorbable materials such as polypropylene or polyester, but resorbable materials such as e.g. poly-p-dioxanone or copolymers of glycolide and lactide are also conceivable. Partularly advantageous is a composite of polypropylene and a copolymer of 90 parts glycolide and 10 parts lactide which is marketed by Ethicon GmbH as warp-knitted mesh under the name "Vypro". Such a composite material has a high strength in the initial period after the surgery, i.e. in the period when the implant is not yet sufficiently grown through by tissue. Subsequently, the resorbable component is decomposed, so that the foreign-body stress on the patient lessens. However, the remaining polypropylene permanently ensures a sufficient and reliable support.

The supports or tapes can contain e.g. polypropylene, but other materials are also conceivable.

BRIEF DESCRIPTION OF THE DRAWINGS

The invention is described in more detail in the following with the help of an embodiment. The drawings show in FIG. 1 a top view of a version of the implant according to the invention and FIG. 2 a perspective schematic view of the implant from FIG. 1 in which the configuration of the implant in the implanted state is indicated.

DETAILED DESCRIPTION

Figure 1:
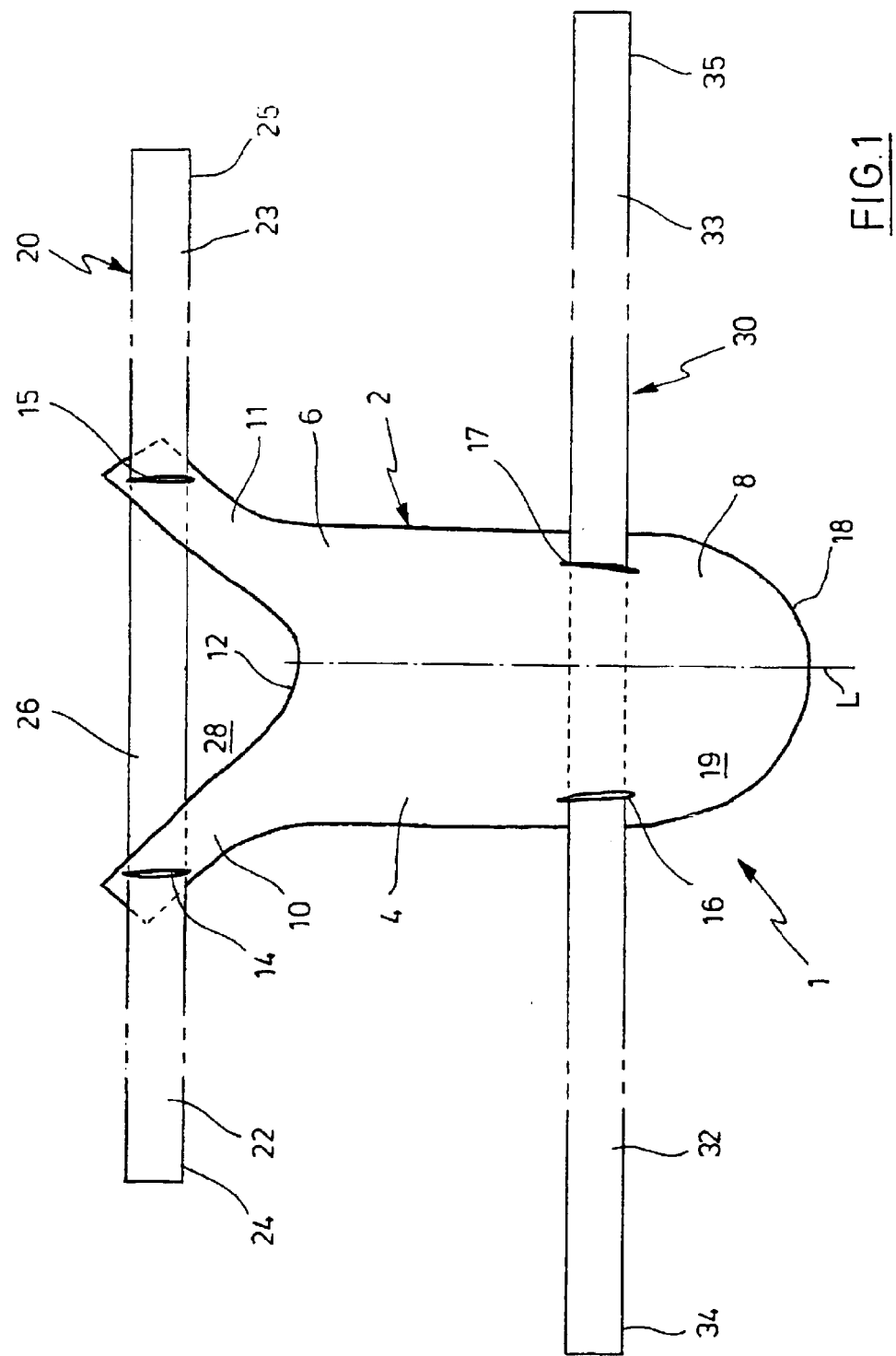
In FIG. 1, a version of an implant 1 is shown in top view. Hidden areas are shown by dotted lines.

The implant 1 has an areal, flexible basic structure 2 which is symmetrical to a longitudinal axis L and consists of a base 4 with a front area 6 and a rear area 8 as well as two extensions 10 and 11. The two extensions 10, 11 start from the front area 6 of the base 4 and extend forwards, as can be seen in FIG. 1. The distance between them increases as they do so. In this way, a concavely rounded front edge 12 develops at the base 4 which merges in a U-shape into the two extensions 10, 11.

In the area of the free end of the extension 10, a slot 14 is provided and a corresponding slot 15 in the free end area of the extension 11. The two slots 14 and 15 are aligned parallel to each other in the embodiment. Two further slots 16 and 17, which are likewise aligned parallel to each other in the embodiment, are located in the rear area 8 of the base 4. The rear area 8 of the base 4 continues rearwards behind the slots 16 and 17 and ends in a convexly rounded rear edge 18. The zone of the base 4 formed behind the slots 16 and 17 is numbered 19 in FIG. 1.

In the embodiment, the basic structure 2 is produced as a polypropylene warp-knitted fabric. If it is cut or punched out from a larger piece of material, its edges as well as the edges of the slots 14, 15, 16 and 17 are preferably treated against unravelling.

Other materials are also conceivable for the basic structure 2, e.g. a composite material with non-resorbable and resorbable parts. An example of such a composite material is a warp-knitted fabric of polypropylene filaments (not resorbable) and filaments from a copolymer of glycolide and lactide in the ratio 90:10 (resorbable). Such a warp-knitted fabric is marketed by the applicant under the name "Vypro".

In the front area of the implant 1, a front tape 20 runs transverse to the longitudinal axis L, which is guided through the two slots 14 and 15 in the extensions 10 and 11. The front tape 20 integrally forms a front support 22 (with a free end 24 on the left side of the longitudinal axis L), a front support 23 (with a free end 25 on the right side of the longitudinal axis L) and a connection 26 which extends between the free end areas of the extensions 10 and 11. The front tape 20 can be moved in the slots 14, 15 which can be advantageous for the progress of the surgery when inserting the implant 1. However, as a rule, the front tape 20 is aligned symmetrical to the basic structure 2.

A free space 28, in which no material of the implant 1 is located, is provided between the connection 26, the two extensions 10 and 11 and the front edge 12 of the base 4.

A rear tape 30 is guided through the two slots 16 and 17, which forms a rear support 32 (with a free end 34 left of the longitudinal axis L) and a rear support 33 (with a free end 35 right of the longitudinal axis L). The rear tape 30 is, just like the front tape 20, movable relative to the base 4, but as a rule is arranged symmetrical to the longitudinal axis L.

In the embodiment, the front tape 20 and the rear tape 30 are made of polypropylene and of a type which can also be used for the tape described at the outset according to WO 96/06567 and WO 97/13465. Preferably, the rear tape 30 is longer than the front tape 20, as indicated in FIG. 1.

Figure 2:
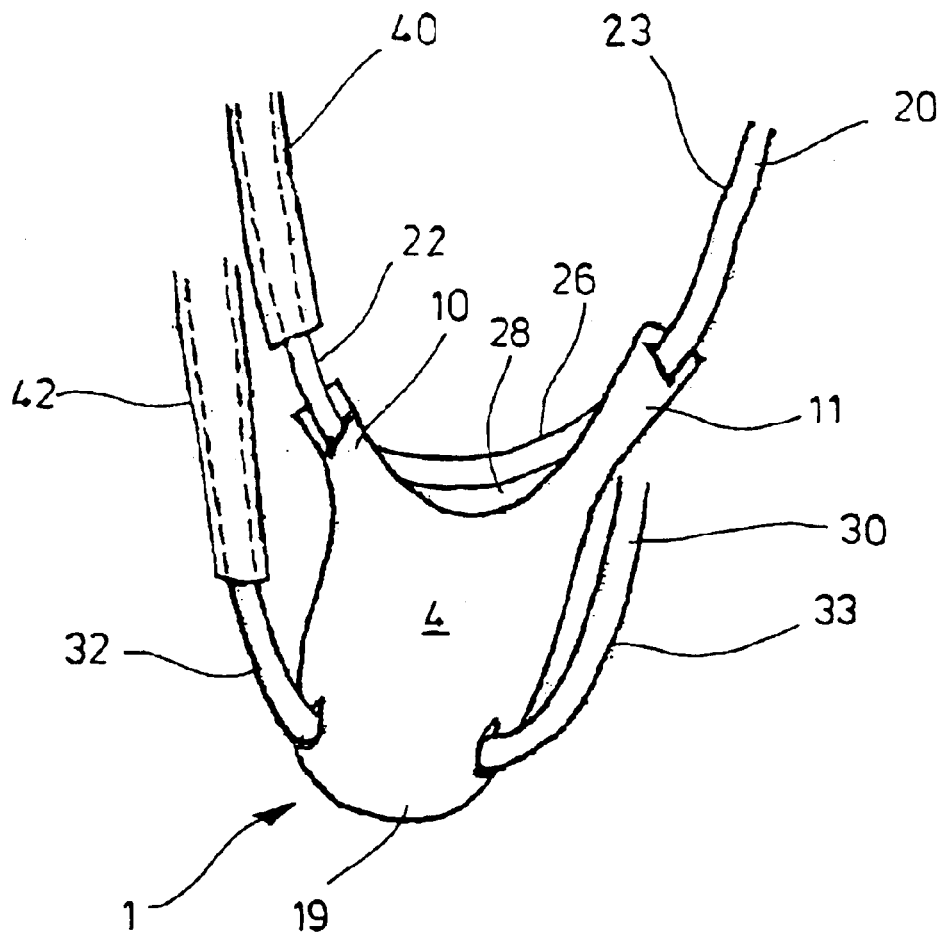

In FIG. 2, the configuration in which the implant is arranged in a patient's body is shown schematically. The base 4 holds the base of the bladder which can be lifted by pulling on the two rear supports 32, 33. The connection 26 supports the mid urethra, but preferably without lying directly against it. The front tape 20 is therefore guided more loosely, as a rule, than is the rear tape 30. The bladder neck is located in the free space 28 and has therefore the mobility necessary for its normal function.

The width of the base 4 measured perpendicular to the longitudinal axis L is preferably approximately 4 cm to 5 cm. Suitable lengths for the front tape 20 and the rear tape 30 are e.g. 45 cm and 50 cm, respectively.

In the embodiment, movable covers (sleeves) 40 and 42, respectively, of a smooth plastics material, are arranged over the front support 22 and the rear support 32, see FIG. 2. Corresponding covers are found on the front support 23 and the rear support 33, but are not shown in FIG. 2, for the sake of clarity.

Furthermore, the free ends 24 of the front support 22 and 34 of the rear support 32 are joined together on delivery of the implant and jointly secured to the shaft of a strong bent surgical needle. Examples of such a needle as well as a grip for guiding the needle are e.g. disclosed in WO 97/13465. The free ends 25 and 35 of the front support 23 and rear support 33, respectively, are likewise jointly secured to a corresponding needle.

With the help of the two needles, the front tape 20 and the rear tape 30 can be efficiently guided through the tissue in the left and right halves of a patient's body until the implant 1 has reached its desired position (see below). The covers 40, 42 facilitate the act of pulling them through the tissue. In order that the surgeon can immediately see which of the tape parts projecting from the body belongs to the front tape 20 and rear tape 30 respectively, the covers 40 and 42 have different colours in the embodiment. When the implant 1 is correctly positioned, the two needles can be separated and the covers 40, 42 pulled off from the front tape 20 and the rear tape 30. The projecting tape parts can then be cut off close to the skin.

In the following, an example of a surgical procedure for inserting the implant 1 is explained in more detail.

The patient is placed in the dorsal lithotomy position and a catheter (e.g. "#18 French Foley") is inserted into the urethra. A vertical vaginal cut is preferably made from the area of the central urethra to the vaginal crown or the cervix (if present). The edges of the cut are gripped with an Allis clamp and pulled back laterally while the surgeon makes a sharp cut directly underneath the vaginal epithelium with Metzenbaum scissors and/or a blunt cut with the index finger. The cut ends when the bone skin (periosteum) is reached and the bladder is free from its vaginal appendages.

Approximately 1 cm laterally and cranially relative to the mons pubis two parallel incisions of approximately 2 cm are made in the suprapubic area. No attempts are made to mobilize the urethra or the bladder neck. In the catheter, a straight insert is positioned to move the urethra and the bladder neck laterally to one side to lessen the risk of injury.

Then a long, bent needle (e.g. as known from WO 96/06567 and WO 97/13465) is inserted laterally to the central urethra into the exposed vaginal wound and directed to the underside of the pubic bone. After perforation of the endopelvic fascia, the needle is guided laterally from the bladder up to the suprapubic incision previously made. If the needle encounters resistance from the rectal fascia, a gentle pressure is exerted on a gripping piece connected to the needle until the needle tip emerges from the suprapubic incision previously made.

After the long, bent needle is pulled out of the incision in the suprapubic area, the end areas of the front tape 20 and of the rear tape 30 project there. The whole process is observed by means of cystoscopy in order to ensure that the urethra and the bladder neck are not injured.

Exactly the same procedure is then carried out on the other side, so that there the opposite end areas of the front tape 20 and of the rear tape 30 project from the incision in the suprapubic area.

Subsequently, the front (anterior) tape 20 and the rear (posterior) tape 30 as well as the flexible basic structure 2 of the implant 1 are positioned. The front tape 20 runs from the abdominal wall on one side round the underside of the central urethra and back to the abdominal wall on the other side. The rear tape 30 likewise starts from the abdominal wall on one side and then runs to the underside of the bladder base and back to the abdominal wall on the other side. In this way, a suspension is effected at four points. The base 4 of the implant is arranged to accommodate the whole bladder with its inside. In order to fix the basic structure 2 in the rear area to the cardial-uterosacral ligament, in order to thus prevent a forward movement of the basic structure 2, two paired sutures are made, e.g. with the suture material marketed by the applicant under the name "Vicryl #2".

If there is an enterocele, the zone 19 of the basic structure 2 is so positioned, after the cutting out of the enterocelic sack, that the defect is closed and is fixed distally from the rectal fascia in order to eliminate a rectouterine pouch. If the zone 19 is not required, it can be cut off.

A gentle pull is now progressively exerted on the rear tape 30 until the bladder is repositioned in its anatomically normal position. The two covers over the rear tape 20 are removed by pulling outward, any increase in the tension of the basic structure 2 during this step having to be prevented, e.g. with the help of tweezers.

Next, the bladder is filled with approximately 300 ml physiological salt solution, and the patient is made to cough (stress test). The two ends of the front tape 20 are pulled simultaneously out of the abdominal incisions until the urine leakage stops. The two covers over the front tape 20 are removed, scissors being placed between the front tape 20 and the periurethral fascia to prevent an increase in the tape tension. The scissors must fit well between the urethra and the front tape 20.

The vaginal cut is closed with a continuous suture of rapidly resorbable suture material (e.g. with the suture material "Vicryl rapid #2.0" marketed by the applicant). It is advisable to cut out as little excess vaginal epithelium as possible; this decreases the risk of a vaginal erosion. Subsequently, a bladder catheter and a vaginal pack remain in the patient for approximately 24 hours.

What is claimed is:

1. An implant for holding the female bladder, comprising:
    an areal, flexible basic structure which has a base with a front area a rear area, and a longitudinal axis running from front to back, and two extensions extending from the front area of the base forwards, the distance between them increasing,
    two front supports extending outwardly from free end areas of the two extensions and with a connection between the free end areas of the two extensions, wherein a free space is formed between the connection, the two extensions and the base, and
    two rear supports extending outwardly from opposite sides in the rear area of the base.

2. The implant according to claim 1, wherein the base has a concavely rounded front edge which merges in a substantially U-shape into the two extensions.

3. The implant according to claim 1, wherein the rear area of the base extends behind the two rear supports and has a convexly rounded rear edge.

4. The implant according to claim 1, further comprising two surgical needles, one needle being attached to a free end of one front support and to a free end of the rear support located on the same side of the longitudinal axis, and the other needle is being attached to a free end of the other front support and to a free end of the other rear support.

5. The implant according to claim 1, further comprising a cover movably arranged on each of the two front supports and the two rear supports.

6. The implant according to claim 1, wherein the two front supports are marked in a different colour from the two rear supports.

7. The implant according to claim 1, wherein the two front supports and the connection are integral and form a front tape.

8. The implant according to claim 7, wherein the front tape passes through a slot in the free end area of one extension and through a slot in the free end area of the other extension.

9. The implant according to claim 7, wherein the two rear supports are integral and form a rear tape.

10. The implant according to claim 9, wherein the rear tape passes through two slots in the rear area of the base.

11. The implant according to claim 9, wherein the front tape is shorter than the rear tape.

12. The implant according to claim 1, wherein the flexible basic structure contains a waft-knitted or warp-knitted fabric.

13. The implant according to claim 1, wherein the flexible basic structure contains at least one material selected from the group consisting of polypropylene, polyester, copolymers of glycolide and lactide, and composites with aforementioned materials.

14. The implant according to claim 1, wherein the supports contain polypropylene.

15. The implant according to claim 1, wherein when the implant is implanted within a female patient's body, the connection between the free end areas of the front support extensions extends beneath and in proximity to the mid-urethra, the bladder neck is positioned within the free space formed between the connection, the two front support extensions, and the base, and the base is positioned beneath and supports the base of the bladder.

16. A method for implanting an implant for holding a female bladder, comprising:
    providing an implant having an areal, flexible basic structure having a base with a front area, a rear area, and a longitudinal axis running from front to back, and two extensions extending from the front area of the base, the implant further having two front supports extending outwardly from free end areas of the two extensions respectively, and a connection extending between the free ends areas, wherein an opening is formed between the connection, the two extensions, and the base, the implant further having two rear supports extending outwardly from opposite sides in the rear area of the base;
    coupling a first needle to a free end of one front support and a free end of one rear support located on the same side of the longitudinal axis;
    coupling a second needle to a free end of the other front support and the other rear support;
    passing the first needle and attached supports through the patients body from an incision in the vagina, past and to one side of the urethra, and out through the abdomen;
    passing the second needle and attached supports through the patients body from the incision in the vagina, past and to the other side of the urethra, and out through the abdomen; and
    positioning the implant so that the base is positioned beneath and supports the base of the bladder and the connection between the free end areas of the front support extensions extends beneath and in proximity to the mid-urethra.

17. The method according to claim 16, wherein the positioning step is accomplished by manipulating portions of the front and rear supports that extend out through the abdomen.

18. A method for implanting an implant for holding the female bladder, comprising:
    providing an implant having an areal, flexible basic structure having a base with a front area, a rear area, and a longitudinal axis running from front to back, and two extensions extending from the front area of the base, the implant further having two front supports extending outwardly from the two extensions respectively, and a connection extending between the two extensions, wherein an opening is formed between the connection, the two extensions, and the base, the implant further having two rear supports extending outwardly from opposite sides of the rear area of the base;
    using at least one needle to pass the front and/or rear supports on the same side of the longitudinal axis through the patients body from an incision in the vagina, past and to one side of the urethra, and out through the abdomen;
    using at least one needle to pass the front and/or rear supports on the other side of the longitudinal axis through the patient's body from the incision in the vagina, past and to the other side of the urethra, and out through the abdomen; and
    positioning the implant so that the base is positioned beneath and supports the base of the bladder and the connection between the free end areas of the front support extensions extends beneath and in proximity to the mid-urethra.

19. The method according to claim 18, wherein the positioning step is accomplished by manipulating portions of the front and rear supports that extend out through the abdomen.

* * * * *